Figure 1:
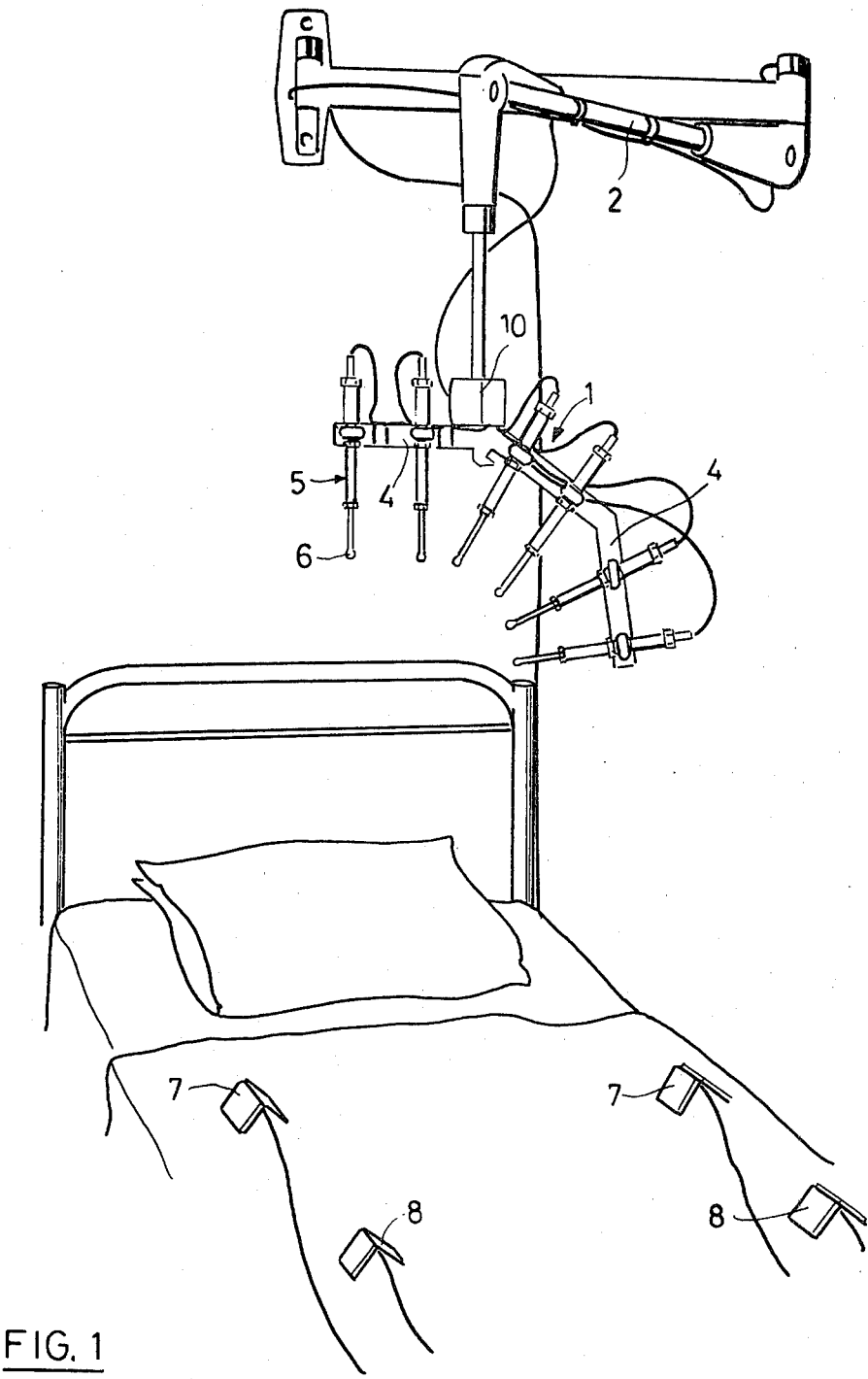

United States Patent [19]

Elmeskog

[11] Patent Number: 4,457,309
[45] Date of Patent: Jul. 3, 1984

[54] ELECTROCARDIOGRAPHIC ELECTRODE DEVICE

[76] Inventor: Alf U. Elmeskog, Minkvägen 13, S-754 60 Uppsala, Sweden

[21] Appl. No.: 355,582
[22] PCT Filed: Jun. 30, 1981
[86] PCT No.: PCT/SE81/00200
 § 371 Date: Feb. 19, 1982
 § 102(e) Date: Feb. 19, 1982
[87] PCT Pub. No.: WO82/00089
 PCT Pub. Date: Jan. 21, 1982

[30] Foreign Application Priority Data

Jun. 30, 1980 [SE] Sweden .................................. 8004804

[51] Int. Cl.³ ............................................... A61B 5/04
[52] U.S. Cl. ............................................... 128/644
[58] Field of Search ................ 128/639, 644, 802, 803

[56] References Cited
U.S. PATENT DOCUMENTS

| 682,089 | 9/1901 | Leach. | |
|---|---|---|---|
| 1,604,585 | 1/1925 | Kennedy. | |
| 2,549,836 | 4/1951 | McIntyre et al. | 128/644 |
| 3,735,753 | 5/1973 | Pisarski | 128/2.1 E |
| 4,062,364 | 12/1977 | Masaki | 128/803 |
| 4,151,836 | 5/1979 | Arnaud et al. | 128/644 |

FOREIGN PATENT DOCUMENTS

| 517356 | 2/1931 | Fed. Rep. of Germany. | |
|---|---|---|---|
| 2748583 | 2/1979 | Fed. Rep. of Germany. | |
| 2831412 | 1/1980 | Fed. Rep. of Germany. | |
| 1051065 | 1/1954 | France | 128/639 |
| 1355600 | 2/1964 | France | 128/644 |
| 7143641 | 7/1973 | France. | |

OTHER PUBLICATIONS

Kneppo et al., "Integral ... Coordinator", IEEE Trans. BioMed. Eng., BME-26, No. 1, Jan. 1979, pp. 21–28.

Primary Examiner—Lee S. Cohen
Attorney, Agent, or Firm—Bacon & Thomas

[57] ABSTRACT

The invention relates to a device for placing electrocardiographic electrodes on a patient's chest, comprising a substantially bow-shaped electrode holder (4), which is at least vertically adjustable, and a number of individually position-adjustable electrodes (5), pivotably carried by the electrode holder (4) and spaced along the same, each electrode (5) being resiliently displaceable towards the electrode holder (4), such that, after adjustment of the electrodes (5), by moving the electrode holder (4) towards the patient's chest the electrodes (5) can be brought to contact the patient's skin at predetermined contact points substantially independently of the patient's thorax configuration.

8 Claims, 3 Drawing Figures

ELECTROCARDIOGRAPHIC ELECTRODE DEVICE

The present invention relates to a new electrocardiographic electrode device, and more particularly to a device for quick and simple application of contact electrodes to the thorax of a patient.

When performing electrocardiography the potentials generated in the heart are sensed by electrodes placed on the body surface according to various diversion systems. The potentials are recorded as wave forms of a characteristic appearance, a so-called electrocardiogram (ECG). Normally, electrodes are placed around the thorax at certain anatomically defined points of measuring and on the extremities. A usual coupling comprises six thorax electrodes and one electrode on each arm and leg. The electrodes consist of metal plates, which are applied against the skin site in question via an electrically conductive electrode paste. To fix the electrodes, it is, as far as the extremity electrodes are concerned, customary to paste them by tape or fasten them by wrist and ankle straps, respectively. As to the thorax electrodes or the so-called pre-cordial electrodes they may also be pasted fast by tape, but the currently most used thorax electrodes are designed with suction cups having a compressible rubber ball, such that they can be made to suck fast to the skin. Although these suction electrodes permit a quicker application, they have several disadvantages. Thus, the risk of incorrect mutual positioning of the electrodes remains (despite colour marking of the cables), and, further, it is difficult to fix the electrodes to elderly persons, whose skin has lost its elasticity, so that the electrodes can fall off during the measurement. Often it is also necessary to shave off a hairy tegument of the chest to make the suction cups adhere properly.

Various devices having fixed thorax electrodes have been proposed to permit a quicker and simplified recording of electrocardiograms. Thus, DE-OS 2748583 discloses a band of a non-conducting material, adapted to be fastened over the chest, the desired number of electrodes being arranged at predetermined positions on the band. The adaptation to different thorax configurations is made possible by the band being extensible. It has, however, turned out to be difficult to make a band which can be adapted to a more extensive variation of thorax configurations, and it has, besides, not involved such advantages that it has replaced the use of the above mentioned suction electrodes to any greater extent.

According to the invention an electrocardiographic device for application of precordial electrodes is suggested, which is simple to use, permits application of the electrodes in the desired positions and eliminates the risk of mutual miscoupling of the electrodes. The device according to the invention comprises an elongate holder or bow, which is at least vertically adjustable through mounting to e.g. a conventional articulated supporting arm. The holder carries a number of electrode means, which project under the same and the free end portions of which form contact-electrode surfaces. The electrode means are resiliently displaceable towards the electrode holder, and the holder and the electrode means are designed such that the contact-electrode surfaces are pressed against the desired anatomic points on the thorax, when the holder is brought towards the chest. Since the electrode means are resiliently mounted, optimum contact of the electrodes is obtained. Preferably the electrode means are rod-shaped and individually pivotably and rotatably arranged in relation to the holder and securable in an arbitrary position. Hereby the directions of the individual electrodes may be adjusted, such that a correct electrode placing may be obtained for the majority of thorax configurations. A suitable design of the electrode means is a rod or bar provided with an electrode ball, which rod is telescopically arranged in a sleeve member and spring biased against the latter. The above mentioned articulated supporting arm may be attached to the wall to the examination bed or bunk, to a stand column etc., and the electrode holder can therefore at measurement easily be swung towards the patient, and moved aside when it is not used, respectively. The supporting arm with the electrode holder can also be arranged on the ECG apparatus, such that the whole measuring device is portable.

Figure 2:
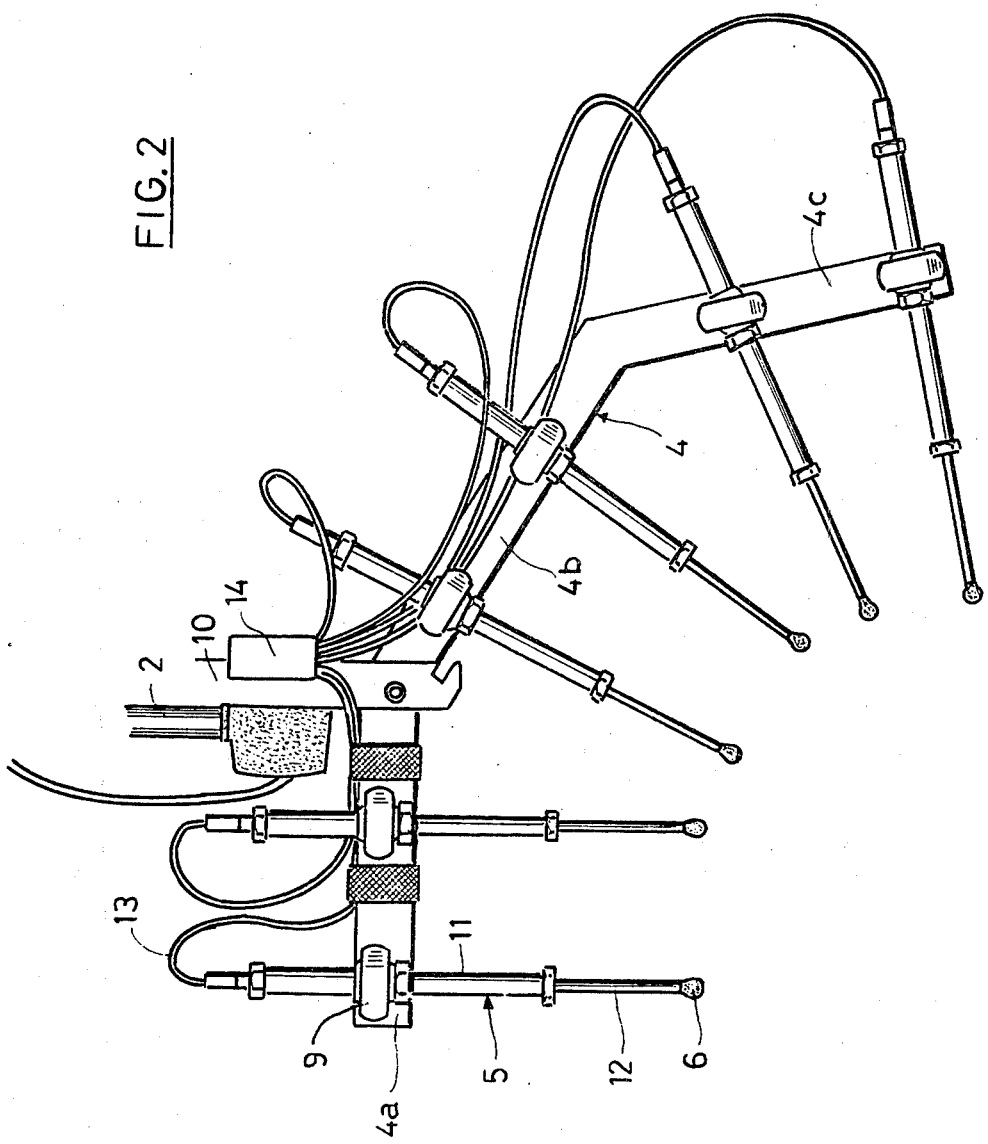
Figure 3:
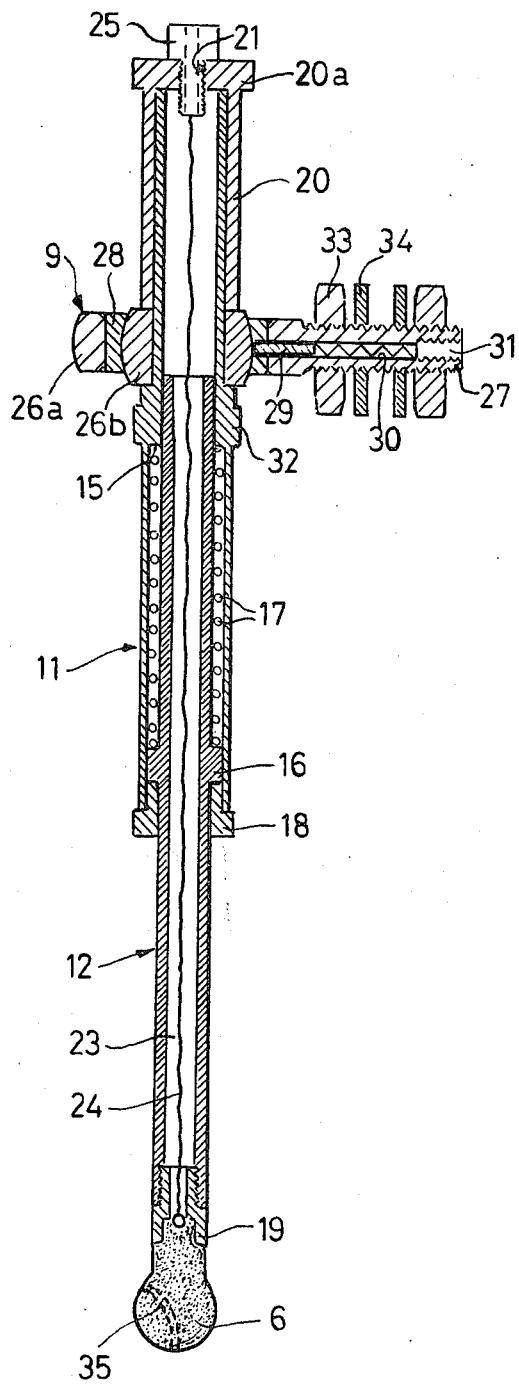

The invention is described in more detail below with respect to a specific embodiment thereof, with reference to the accompanying drawings, wherein FIG. 1 is a perspective view of an embodiment of a device according to the invention placed at an examination bed;

FIG. 2 is a perspective view of the electrode bracket of the device of FIG. 1; and FIG. 3 is a longitudinal section of an electrode means of FIG. 2.

In FIG. 1 an electrode holder 1 is attached to a per se conventional articulated supporting arm 2, which, in the shown case, is attached to the wall above an examination bed. The electrode holder 1 comprises a bow-shaped part 4, carrying six electrode means 5, whose end portions 6 consist of contact electrodes designed to be applied against the patient's thorax. The number of electrode means may, of course, vary depending on the electrocardiographic measuring system used, and e.g. seven or eight electrodes may also be comtemplated. In use-as will be further described below-it is only necessary to bring the electrode holder 1 towards the patients thorax, such that the contact electrodes 6 contact the skin in the desired, anatomically predetermined positions, and to place two pairs of extremity electrodes 7 and 8 on the patient's wrists and ankles, respectively.

The detailed construction of the electrode holder 1 is better shown in FIG. 2. The very holder or bow section 4 is, in the shown case, designed to have three straight sections 4a–4c arranged in angle to each other, such that the bow 4 obtains a suitably curved shape. Each bow segment 4a, 4b, 4c carries two electrode means 5, releasably fixed in horizontal bores in the bow 4. Each electrode means 5 is pivotally jornalled in its holder 9, as will be more explicitly described below. Possibly, the bow 4 is pivoted, e.g. at the transition section between the bow segments 4a and 4b and/or 4b and 4c. Further, the holders 9 may possibly be displaceable along the respective bow sections 4a–4c. The bow segment 4a is in the shown case arranged substantially horizontally. At the transition section to the segment 4b a fastening means 10 is provided for attachment to the supporting arm 2 in a suitable manner.

Each electrode means 5 substantially consists of an upper sleeve section 11, which is fixed in the holder 9, and an electrode rod 12, telescopically arranged in the sleeve 11. The electrode rod 12 is spring-biased in the sleeve 11, such that it can be pressed into the sleeve against the spring force. Each electrode rod 12 comprises, or carries in its end portion, the above mentioned contact electrode 6. Electric cables 13 leading from the upper parts of the electrode means 5 are electrically connected to the contact electrodes 6. The cables 13 are connected to a contact box 14 on the attachment member 10, from where they are connected to the ECG recording apparatus.

An example of how an electrode means 5 may be designed is shown in FIG. 3. As in FIG. 2 it comprises a sleeve section 11 and an electrode rod 12 telescopically mounted therein. In the shown case the upper part of the sleeve section 11 has a smaller inside diameter than the lower part thereof, the transition being indicated at 15. Instead of having different diameters of the sleeve 11, it is also possible to arrange an inwardly projected bulge or flange at 15 in the Figure. The electrode rod 12 is at a suitable location, e.g. near its central part, provided with a projection or bulge portion 16. In the interspace between the sleeve 11 and the electrode rod 12 a coil spring 17 is disposed, the step 15 and bulge 16, respectively, serving as stops for the spring. The rod 12 is retained in the sleeve 11 by the lower part of the sleeve having a smaller diameter than the bulge 16. In the shown case this is achieved by means of a bored hexagon-headed screw 18 or the like, which is threaded into a threaded end part of the sleeve 11. The bore of the screw 18 then corresponds to the diameter of the electrode rod 12. To the end part of the electrode rod 12 an electrode ball 6 is attached, which as in FIG. 3, suitably has a pear-like shape, so that it easily can be wiped off and cleaned. The electrode ball 6, which is of a conducting material, usually argentan, is fixed to the electrode rod 12 through a cylindrical member 19 of an electrically insulating material (e.g. PVC-plastic) having a central through-recess. The attachment may be effected e.g. by providing the upper part of the insulating member or sleeve 19 with an outer threaded section, which fits into a corresponding inner thread of the end portion of the rod 12, and providing the lower part thereof with an inner threaded section, into which a correspondingly threaded section at the upper part of the contact electrode ball can be threaded. The upper part of the sleeve section 11 is provided with an outer sleeve 20, the top part 20a of which is nut-shaped and provided with a bore 21. The outer sleeve 20 is attached to the sleeve 11, e.g. threaded on a correspondingly threaded section of the upper part of the sleeve 11. The electrode rod 12 is provided with a central inner bore or recess 23, through which an electric wire 24, suitably in the form of a spiral wire, runs from the contact electrode 6 to a contact means 25, e.g. the female part of a banana pin inserted, e.g. threaded, into the bore or hole 21 of the upper part of the top sleeve 22. The contact means 25 is arranged such that it can be brought into electric contact with a corresponding contact means (e.g. the male part of a banana pin) at the end of the cable 13 of FIG. 2. The spiral wire 24 is suitably attached to the electrode ball through soldering.

As mentioned above each electrode means 5 is carried by the bow 1 through a holder 9, which may be arranged as in FIG. 3. Here, the holder 9 comprises a ring portion 26, which carries the electrode means 5, and a shaft portion 27, which is fixed in a corresponding bore of the bow 4. The ring portion 26 is of the ball-joint type and comprises an outer ring 26a and a ball-shaped inner ring 26b, adapted to embrace and carry the electrode means 5. The ball ring 26b is turnably and pivotably journalled in the outer ring 26a, possibly via a friction layer 28. Hereby it is steplessly adjustable in the outer ring, such that the contact electrodes 6 of the electrode means 5 can be set in an arbitrary position within a circular area, the size of which thus depends on the length and maximum pivot angle of the electrode means 5. The ball 26b may be fixed in a desired position by means of locking means acting upon the ball. Said means may, e.g. as in FIG. 3, consist of a pin 29 or the like of a suitable material, which is slidably mounted in a central bore 30 in the shaft portion 27 of the holder 9. The pin 29, which e.g. may be of plastic, is displaceable in the bore 30 by means of a screw means 31 (e.g. an Allen screw) in the threaded end portion of the bore 30. The pin is suitably made in two parts with an intermediate spring to facilitate the adjustment of a desired compressive force. The sleeve 11 of the electrode means 5 is fitted into the bore of the inner ring 26b retained, on one hand, by an outer bulge-shaped portion 32 of the sleeve 11, and, on the other hand, by the lower edge of the outer sleeve 20, the length of which is adjusted with regard to the thickness of the holder 9. The shaft portion 27 of the holder 9 is threaded and adapted to be inserted into the previously mentioned bores of the bow 4. The holder 9 is fixed in a desired position in the bow by means of a nut 33 and a washer 34 on one side of the box, and corresponding members on the other side of the bow. In order to facilitate the screwing in and on of the screw member 18 and the outer sleeve 20, respectively, the lower part of the bulge portion 32 of the sleeve 11 is suitably nut-shaped, e.g. hexagonal. Preferably, one or more guide means (not shown) are arranged to prevent the electrode rod 12 from turning in the sleeve 11. Said means may e.g. consist of a pin, which is fixed to the sleeve 11, suitably in the bulge portion 32, and which cooperates with a longitudinal slit of the electrode rod 12.

By suitably selecting the shape and position of the holders 9 in the bracket 4, a placing of the contact electrodes 6 may be achieved which is roughly adapted to the majority of thorax configurations. An individual adjustment to each patient is then performed by pivoting and/or rotating one or more of the electrode means 5 in the holder 9, after the screw means 31 has been undone.

When an electrocardiogram is to be picked up, electrode paste is applied on the contact electrode surfaces, i.e. the contact electrodes 6 of the electrode means 5 and the extremity electrodes 7 and 8, in conventional manner. Then, the electrodes 7 and 8, the electrode surfaces of which, in the shown case, consist of V-shaped metal plates, are placed on the wrists and ankles of the patient, and the electrode holder 1 is brought down towards the patient's chest. When necessary, the inclination setting of one or more of the electrode means 5 is adjusted by undoing the screw means 31, such that the respective electrode means 5 and the surrounding ball member 26b of the holder 9 can be turned in relation to the outer ring 26a. Then, the electrode means is fixed in the desired position. When the electrode holder 1 subsequently is applied against the chest, all the electrodes 6 are accurately placed and are retained fixed against the thorax through the action of the spring means 17, acting between the sleeve 11 and electrode rod 12 of the electrode means 5. The spring pressure is adjusted, such that the patient is permitted to breath normally. When measurement is completed, the electrode holder 1 is brought upwards and aside through the pivoted supporting arm 2. Thus, through the above described electride device a considerably simplified and quick measurement procedure is achieved, wherein the correct order of the electrodes is always obtained.

The material of the parts which have no conducting or insulating function is not critical per se, but with regard to alternating-current disturbancies it may be suitable to form, for example, the electrode bow 4 of a plastic material.

Instead of smearing electrode paste onto the contact electrode surfaces, special electrode paste strips may be used, which are pasted on before each measurement. According to another variant, the electrode ball 6 of FIG. 3 may be provided with a passage or bore (dashed in FIG. 3 at 35), which through a tube is connected to a central container for electrode paste. It is then possible to press out electrode paste to all the contact electrodes 6 through one single manoeuvre.

The invention is, of course, not restricted to the embodiment specifically described above and shown in the drawings, but many variations and modifications are possible within the scope of the subsequent claims. Thus, e.g. the construction of the electrode means 5, as well as the mounting or fastening thereof in the bow 4, as well as the bow shape may be varied considerably.

I claim:

1. A support and adjustment device for applying electrocardiographic electrodes to the thorax of a patient comprising: (a) an elongate, substantially bow-shaped electrode holder; (b) support means attached to the electrode holder such that the electrode holder is, adjustable in at least a vertical direction; (c) a plurality of electrodes having resiliently disposed contact portions; (d) attachment means pivotally connecting each of the electrodes to said electrode holder at spaced apart intervals such that each of said electrodes is pivotally adjustable and resiliently displaceable with respect to said electrode holder to enable each of the electrodes to contact a patient's skin at predetermined contact points substantially independent of said patient's thorax configuration; and (e) electrical connecting means for connecting each of the electrodes with a monitoring device.

2. A device according to claim 1, wherein the attachment means includes pivoting means such that each of said electrodes is pivotable in at least the longitudinal and transverse directions with respect to the electrode holder.

3. A device according to claim 2, wherein the attachment means comprises a rotary ball-type joint.

4. A device according to claim 1, wherein the electrodes are substantially rod-shaped.

5. A device according to claim 4, wherein each of said plurality of electrodes comprises a sleeve portion and a rod portion telescopically mounted in the sleeve portion.

6. A device according to claim 5, further comprising spring means interposed between the sleeve portion and the rod portion such that the rod portion is displaceable therein, the rod portion having a free end portion which comprises the contact portion of the electrode.

7. A device according to claim 6, further comprising insulating means to electrically insulate the contact portion of the electrode from the rod portion; a second contact portion in the sleeve portion of the electrode; and lead means connecting the second contact portion in the sleeve portion with the contact portion of the electrode on the free end of the rod portion.

8. A device according to claim 1, wherein each of the contact portions of the electrodes define an aperture to allow passage of electrode paste.

* * * * *